(12) United States Patent
Chen et al.

(10) Patent No.: US 11,878,085 B2
(45) Date of Patent: Jan. 23, 2024

(54) LED UV STERILIZATION DEVICE

(71) Applicants: Shanghai Sansi Electronic Engineering Co. Ltd., Shanghai (CN); Shanghai Sansi Technology Co. Ltd., Shanghai (CN); Jiashan Sansi Optoelectronic Technology Co. Ltd., Country Jiaxing (CN); Pujiang Sansi Optoelectronic Technology Co. Ltd., Jinhua (CN)

(72) Inventors: Ming Chen, Shanghai (CN); Xiaoliang He, Shanghai (CN); Shan Li, Shanghai (CN); Defeng Ni, Shanghai (CN)

(73) Assignees: Shanghai Sansi Electronic Engineering Co. Ltd., Shanghai (CN); Shanghai Sansi Technology Co. Ltd., Shanghai (CN); Jiashan Sansi Optoelectronic Technology Co. Ltd., Zhejiang (CN); Pujiang Sansi Optoelectonic Technology Co. Ltd., Zhejiang (CN)

( * ) Notice: Subject to any disclaimer, the term of this patent is extended or adjusted under 35 U.S.C. 154(b) by 0 days.

(21) Appl. No.: 17/840,648

(22) Filed: Jun. 15, 2022

(65) Prior Publication Data
US 2023/0126492 A1   Apr. 27, 2023

(30) Foreign Application Priority Data
Oct. 22, 2021   (CN) .......................... 2021225597479

(51) Int. Cl.
*A61L 2/10*   (2006.01)
*F21V 3/06*   (2018.01)
(Continued)

(52) U.S. Cl.
CPC ................ *A61L 2/10* (2013.01); *F21V 3/061* (2018.02); *F21V 23/003* (2013.01); *H05B 47/115* (2020.01); *F21Y 2115/10* (2016.08)

(58) Field of Classification Search
CPC .......... A61L 2/01; F21V 3/061; F21V 23/003; H05B 47/115
See application file for complete search history.

(56) References Cited

U.S. PATENT DOCUMENTS 9,540,252 B1 * 1/2017 Collins .................... A61L 2/10
9,764,050 B1 * 9/2017 Almeida .................. A61L 2/24
(Continued)

*Primary Examiner* — Bryon T Gyllstrom
(74) *Attorney, Agent, or Firm* — IPRTOP LLC

(57) ABSTRACT

An LED UV sterilization device, including a lens assembly and a light source assembly; the lens assembly includes a plurality of lenses of different materials suitable for light of different wavelengths; the light source assembly includes a visible light source assembly and an ultraviolet light source assembly. Visible light irradiated by the visible light source assembly and invisible ultraviolet light irradiated by the ultraviolet light source assembly pass through lenses of corresponding materials and form an overlapped light spot, so that an irradiation location of the invisible ultraviolet light is indicated by the visible light. The LED UV sterilization device not only realizes safe disinfection and sterilization, but also visualizes the sterilization process. The sterilization process is safer and more reliable, and the sterilization area is more accurate.

7 Claims, 2 Drawing Sheets

(51) Int. Cl.
*H05B 47/115* (2020.01)
*F21V 23/00* (2015.01)
*F21Y 115/10* (2016.01)

(56) References Cited

U.S. PATENT DOCUMENTS

| | | | |
|---|---|---|---|
| 2007/0086912 A1* | 4/2007 | Dowling | C02F 1/325 422/1 |
| 2009/0175041 A1* | 7/2009 | Yuen | F21V 3/061 362/373 |
| 2016/0083271 A1* | 3/2016 | Chen | A61L 2/10 250/432 R |
| 2016/0137276 A1* | 5/2016 | Salters | A61L 2/10 114/222 |
| 2017/0045198 A1* | 2/2017 | Ruiz De Apodaca Cardeñosa | H01L 33/52 |
| 2017/0290933 A1* | 10/2017 | Collins | A61L 9/20 |
| 2017/0348445 A1* | 12/2017 | Bogdanovich | F21V 5/007 |
| 2021/0063007 A1* | 3/2021 | Khalifa | F21V 29/74 |

\* cited by examiner

LED UV STERILIZATION DEVICE

CROSS REFERENCE TO RELATED APPLICATION

This application claims the benefits of priority to Chinese Patent Application No. CN 2021225597479, entitled "LED UV STERILIZATION DEVICE", filed with CNIPA on Oct. 22, 2021, the contents of which are incorporated herein by reference in its entirety.

BACKGROUND

Field of Disclosure

The present disclosure relates to the field of ultraviolet sterilization technology, and in particular, to an light emitting diode (LED) ultraviolet (UV) sterilization device.

Description of Related Arts

In the context of global epidemic of COVID-19, a variety of sterilization products are emerging, and ultraviolet irradiation has become a common way to sterilize. However, as the market generally uses ultraviolet light with wavelengths of 100~400 nm (invisible to the naked eye), there are often certain safety risks during the disinfection process, such as easy injury to human body or incomplete disinfection.

Studies have shown that UV radiation mainly disinfects microorganisms (bacteria, viruses, bacteriophages and other pathogens) by causing them to die through radiation damage and destruction of their nucleic acid function. The effect of UV radiation on nucleic acids can lead to the breakage of bonds and chains, cross-linking between strands and the formation of photochemical products, etc., thus altering the biological activity of DNA and preventing microorganisms from replicating themselves. This UV damage is also fatal. Traditional UV sterilization lamps are extremely harmful to the human body in case of misuse, and should be used when no one is around. If a person inadvertently enters a sterilization area of the sterilization lamp during its use, it will cause damage to the human body.

SUMMARY

The present disclosure provides an LED UV sterilization device.

The LED UV sterilization device includes a lens assembly and a light source assembly; the lens assembly includes a plurality of lenses of different materials suitable for light of different wavelengths; the light source assembly includes a visible light source assembly and an ultraviolet light source assembly. Visible light irradiated by the visible light source assembly and invisible ultraviolet light irradiated by the ultraviolet light source assembly pass through lenses of corresponding materials and form an overlapped light spot, so that an irradiation location of the invisible ultraviolet light is indicated by the visible light.

In an embodiment of the present disclosure, the lens includes a first lens and a second lens; the first lens is used for visible light transmission, and the material of the first lens includes any one of polycarbonate (PC), polymethyl methacrylate (PMMA), and glass; the second lens is used for ultraviolet light transmission, and the material of the second lens includes quartz glass.

In an embodiment of the present disclosure, the visible light source assembly includes a visible light chip; the ultraviolet light source assembly includes one or more of a UVA chip, a UVB chip, and a UVC chip.

In an embodiment of the present disclosure, the ultraviolet light source assembly includes a UVA chip and a UVC chip; the lens assembly is reserved with an accommodating space for placing a UVC lens suitable for the UVC chip.

In an embodiment of the present disclosure, the LED UV sterilization device further includes a human body sensing component and a control component. The control component is electrically connected to the human body sensing component. When the human body sensing component senses human body information, the information is fed back to the control component, so that the control component controls the ultraviolet light source assembly not to emit UV light.

In an embodiment of the present disclosure, an operating mode of the LED UV sterilization device includes an illumination mode, a sterilization mode, and a visible sterilization mode. In the illumination mode, the visible light source assembly emits visible light; in this mode, the control component does not respond when the human body sensing component senses human body information. In the sterilization mode, the ultraviolet light source assembly emits ultraviolet light; in this mode, the control component turns off the ultraviolet light source assembly when the human body sensing component senses human body information. In the visible sterilization mode, the visible light source assembly emits visible light, and the ultraviolet light source assembly emits ultraviolet light; in this mode, the control component turns off at least the ultraviolet light source assembly when the human body sensing component senses human body information.

In an embodiment of the present disclosure, the human body sensing component includes an infrared sensor and/or a radar sensor.

In an embodiment of the present disclosure, the light source assembly further includes a ceramic heat sink, at least one chip of the light source assembly is provided on the ceramic heat sink.

In an embodiment of the present disclosure, the LED UV sterilization device further includes a lamp housing assembly and a lamp cap assembly.

As mentioned above, the LED UV sterilization device of the present disclosure has the following beneficial effects:

1. Visible light provides indications during the operation of UV light, thus improving the safety and effectiveness of disinfection and sterilization.

2. Ultraviolet light with multiple wavelengths are used for disinfection and sterilization, providing better disinfection effect.

3. The substrate of the light source assembly is made of ceramic material, which can better dissipate heat, insulate and resist corrosion.

4. The sensor is set to enhance safety performance.

DETAILED DESCRIPTION OF THE PRESENT DISCLOSURE

Figure 1:
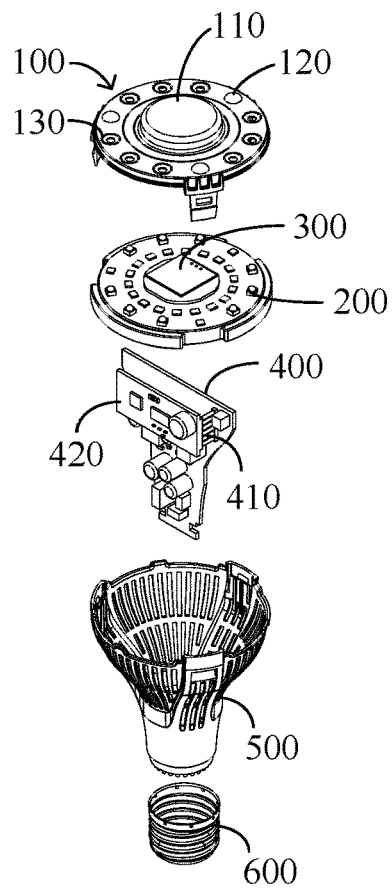
FIG. 1 is an exploded view of an LED UV sterilization device according to an embodiment of the present disclosure.

The embodiments of the present disclosure will be described below through exemplary embodiments. Those skilled in the art can easily understand other advantages and effects of the present disclosure according to contents disclosed by the specification. The present disclosure can also be implemented or applied through other different exemplary embodiments. Various modifications or changes can also be made to all details in the specification based on different points of view and applications without departing from the spirit of the present disclosure. It needs to be stated that the following embodiments and the features in the embodiments can be combined with one another under the situation of no conflict.

It should be understood that the structures, proportions, sizes, and the like, which are illustrated in the drawings of the present specification, are only used to clarify the contents disclosed in the specification for understanding and reading by those skilled, and are not intended to limit the implementation of the present disclosure, thus are not technically meaningful. Any modification of the structure, change of the scale, or adjustment of the size should still fall within the scope of the technical contents disclosed by the present disclosure without affecting the effects and achievable objectives of the present disclosure. In the meantime, the terms "upper", "lower", "left", "right", "middle", "horizontally" and "longitudinally" as used herein, which indicate the orientation or position relationship, are only for convenience of description, and are not intended to limit the scope of the present disclosure, and the change or adjustment of the relative relationship is considered to be within the scope of the present disclosure without substantial changes in technology.

In addition, the terms "first" and "second" are used only to distinguish between different objects, and cannot be understood as indicating or implying relative importance or implicitly indicating the number of indicated technical features. Thus, the features defined with "first" and "second" may explicitly or implicitly include one or more of these features. The meaning of "a plurality of" means two or more, unless otherwise specifically defined.

In the present disclosure, unless otherwise clearly specified and limited, the terms "install", "connect", "couple", "fix" and other terms should be understood in a broad sense. For example, it can be a fixed connection, a detachable connection, or be integral. It can be a mechanical connection, or an electrical connection. It can be a direct connection, or indirect connection through an intermediate medium, or it can be an internal connection between two components or interaction between two components. Those of ordinary skill in the art can understand the specific meanings of the above terms in the present disclosure according to specific situations.

It needs to be stated that the drawings provided in the following embodiments are just used for schematically describing the basic concept of the present disclosure, thus only illustrating components only related to the present disclosure and are not drawn according to the numbers, shapes and sizes of components during actual implementation, the configuration, number and scale of each component during actual implementation thereof may be freely changed, and the component layout configuration thereof may be more complex.

The present disclosure provides an LED UV sterilization device. The LED UV sterilization device of the present disclosure will be described in detail below in combination with specific embodiments.

FIG. 1 shows an exploded view of an LED UV sterilization device according to an embodiment of the present disclosure. The LED UV sterilization device includes: a lens assembly 100, a light source assembly 200, a human body sensing component 300, and a power supply assembly 400.

Specifically, the lens assembly 100 includes a plurality of lenses of different materials suitable for light of different wavelengths, for example, the lens assembly 100 includes a first lens 110 and a second lens 120. The first lens 110 can transmit visible light and is made of any one of polycarbonate (PC), polymethyl methacrylate (PMMA), glass and silicone. Preferably, since PC is more heat-resistant, impact-resistant, flame-resistant, and environmentally friendly than PMMA, the first lens 110 is preferably a PC lens. The second lens 120 can transmit ultraviolet light, and the material of the second lens 120 includes quartz glass, UV-transmitting black glass, soda-lime-silica short-wave UV transmitting glass and soda-lime UV-transmitting glass. Preferably, the second lens 120 is made of quartz glass, because quartz glasses have the advantages of high temperature resistance, good corrosion resistance, good thermal stability, and good light transmission performance.

It should be noted that the first lens 110 and the second lens 120 may be integrated as a whole or may be separated structures.

Figure 2:
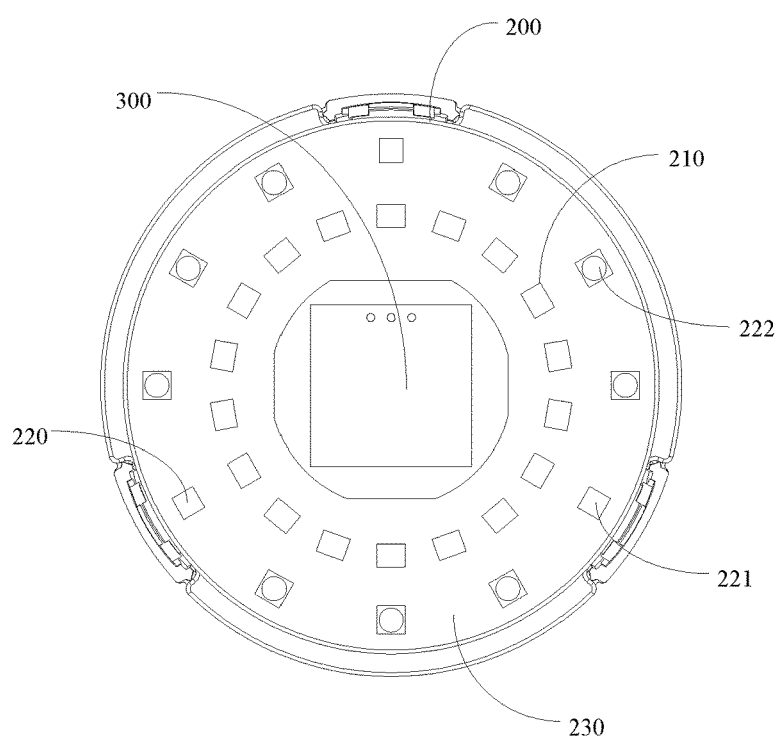
FIG. 2 is a schematic diagram showing the top section of an LED UV sterilization device according to an embodiment of the present disclosure.

FIG. 2 is a schematic diagram showing the top section of an LED UV sterilization device according to an embodiment of the present disclosure.

Specifically, the light source assembly 200 includes a visible light source assembly 210 and an ultraviolet light source assembly 220. Visible light refers to a part of the electromagnetic spectrum that can be perceived by the human eye, and the wavelength of visible light ranges from 400 to 780 nm; ultraviolet light belongs to invisible light, which cannot be perceived by the human eye, and the wavelength of ultraviolet light ranges from 100 to 400 nm. The visible light source assembly 210 includes a visible light chip; the ultraviolet light source assembly 220 includes one or more of a UVA chip, a UVB chip, and a UVC chip. Visible light irradiated by the visible light source assembly 210 and invisible ultraviolet light irradiated by the ultraviolet light source assembly 220 pass through lenses of corresponding materials and form an overlapped light spot, thereby indicating the irradiation location of the invisible UV light through the visible light. For example, the light emitted by the visible light source assembly 210 and passing through the first lens 110 forms an overlapped light spot with the light emitted by the ultraviolet light source assembly 220 and passing through the second lens 120.

At this time, the visible light can be used to determine the irradiation area of ultraviolet light, thus making the sterilization effect more effective and fast.

It is worth noting that, since ultraviolet light is invisible to naked eyes, traditional UV sterilization lamps often have certain safety hazards in the disinfection and sterilization process, such as easy injury to human body and incomplete disinfection. By combining the use of visible light chip, the LED UV sterilization device provided by the present disclosure allows visible light to indicate the irradiation area of ultraviolet light, thus visualizing the sterilization process. As a result, not only the sterilization efficiency is improved, but also the disinfection effect is more thorough.

It should be noted that the visible light source assembly 210 is mainly used to convert electrical signals into light signals, and the visible light is used for illumination. The visible light chip may be a semiconductor LED chip or a laser diode (LD) chip. The visible light chip of this embodiment preferably uses an LED chip, for reasons below: LED chips are in the form of secondary optical design, which endows them with higher lighting efficiency, longer service life, and higher safety.

It should be noted that the ultraviolet light source assembly 220 is mainly used to convert electrical signals into light signals, and the ultraviolet light is used for sterilization. The ultraviolet light source assembly 220 includes one or more of a UVA chip, a UVB chip, and a UVC chip. The combination includes: only one of UVA chip, UVB chip and UVC chip is used; any two of UVA chip, UVB chip and UVC chip are used; all of UVA chip, UVB chip, and UVC chip are used. All of the above combinations of uses are within the protection scope of the present disclosure. It is known that UVC band has the strongest sterilizing effect among UV light. Therefore, a UVC chip is mainly selected for the ultraviolet light source assembly 220. And because the combination of multiple wavelengths can make the sterilization effect better and more thorough, and UVB wavelengths are commonly used in the treatment of skin diseases, when multiple wavelengths are combined to sterilize, the UVC chip and the UVA chip are preferred for the ultraviolet light source assembly 220.

Specifically, the light source assembly 200 further includes a ceramic heat sink 230. At least one set of the visible light source assembly 210 and the ultraviolet light source assembly 220 is placed on top of the ceramic heat sink 230. The ceramic heat sink 230 endows the visible light source assembly 210 and the ultraviolet light source assembly 220 with better heat dispersion, insulating performance and corrosion resistance.

Specifically, the LED UV sterilization device of the present disclosure further includes a human body sensing component 300 and a power driving assembly 400. The human body sensing component 300 may be any one of a variety of sensors such as infrared sensors, radar sensors, motion sensors, etc., to sense the presence of the human body to avoid UV damage to the human body. The power driving assembly 400 includes a power supply component 410 and a control component 420; the control component 420 may be an Advanced RISC Machine (ARM) controller, a Field Programmable Gate Array (FPGA) controller, a System on Chip (SoC) controller, a Digital Signal Processing (DSP) controller, or a Microcontroller Unit (MCU) controller. The control component 420 may be electrically connected to the power supply component 410 and the human body sensing component 300, so as to control the working mode of the LED UV sterilization device and the switch of power supply. For example, when the human body sensing component 300 senses human body information, the information is fed back to the control component 420, so that the control component 420 controls the ultraviolet light source assembly 220 not to emit UV light.

In some embodiments, the control component 420 controls the on and off of the power supply component 410 by receiving the information fed by the human body sensing component 300, to enable different operating modes of the LED UV sterilization device, including a illumination mode, a sterilization mode, and a visible sterilization mode:

1) in the illumination mode, the control component 420 controls the visible light source assembly 210 to emit visible light; in this mode, the control component 420 does not respond when the human body sensing component 300 senses information from a human body or other living creatures, i.e., movements of a human body or other living creatures do not affect the operation of this mode.

2) in the sterilization mode, the control component 420 controls the ultraviolet light source assembly 220 to emit ultraviolet light; in this mode, the control component 420 turns off the ultraviolet light source assembly 220 when the human body sensing component 300 senses information from a human body or other living creatures, i.e., movements of a human body or other living creatures will affect the operation in this mode; the timely shutdown of the ultraviolet light source assembly 220 when information about the human body or other living creatures is sensed can effectively prevent the UV light from causing harm to the human body or other living creatures.

(3) in the visible sterilization mode, the control component 420 controls the visible light source assembly 210 to emit visible light and controls the ultraviolet light source assembly 220 to emit ultraviolet light; in this mode, when the human body sensing component 300 senses information from a human body or other living creatures, the control component 420 turns off at least the ultraviolet light source assembly 220.

It is to be noted that in the sterilization mode, the control component 420 may also control the operation mode of the ultraviolet light source assembly 220 according to the composition of the ultraviolet light source assembly 220 of the LED UV sterilization device. For example, when the ultraviolet light source assembly 220 consists of a UVA chip, a UVB chip, and a UVC chip, the control component 420 controls the ultraviolet light source assembly 220 to achieve the following operation modes: any one of the three works alone; any two of the three work in combination; the three work together.

It should be noted that the control component 420 and the power supply component 410 may be two separate components connected to each other, or may be integrated as a whole. Specifically, the control component 420 and the power supply component 410 may be separate components that are connected via a power supply fixing plate, which saves space and facilitates control. Alternatively, the control component 420 may be integrated inside the power supply component 410, for example by securing the two via a PIN pin, to further save space.

It is worth noting that the LED UV sterilization device provided by the present disclosure is a hardware device, which can be used alone or in combination with some existing software or programs, but the present disclosure does not involve any update of software technology.

For ease of understanding, the combination of a visible light chip with UV chips of multiple wavelengths, and the combination of a visible light chip with a single UV chip, respectively, are further illustrated below.

Embodiment 1: The Combination of a Visible Light Chip with UV Chips of Multiple Wavelengths, Specifically "Visible Light Chip+UVA Chip+UVC Chip" as an Example Specifically, as shown in FIG. 2, the light source assembly 200 includes a visible light source assembly 210, an ultraviolet light source assembly 220, and a ceramic heat sink 230. The visible light source assembly 210 includes a visible light chip 211; the ultraviolet light source assembly 220 includes a UVA chip 221 and a UVC chip 222, where the UVC chip 222 includes a special UVC lens. At this time, as shown in FIG. 1, the lens assembly 100 is provided with an accommodating space 130 for placing the UVC lens; the visible light chip 211, the UVA chip 221, and the UVC chip 222 are placed on the ceramic heat sink 230.

In some embodiments, the visible light chip 211 is an LED chip, the first lens 110 is preferably a PC lens, the visible light emitted by the LED chip passes through the PC lens to form a visible beam a; the second lens 120 is preferably quartz glass, the ultraviolet light emitted by the UVA chip 221 passes through the quartz glass to form an ultraviolet beam b; the ultraviolet light emitted by the UVC chip 222 passes through the UVC lens placed at the accommodating space 130 to form an ultraviolet beam c. The three beams (a, b and c) converge to form an overlapped spot on the surface to be irradiated (i.e., the area to be sterilized). At this time, visible light will indicate the irradiation position of the ultraviolet light, thus making the sterilization effect more effective and fast.

It should be noted that the UVC lens, the first lens 110, and the second lens 120 may be integrated as a whole or may be separated structures. Specifically, when the UVC lens, the first lens 110 and the second lens 120 are integrally formed as a lens 100, the first lens 110, i.e., the PC lens, is placed at the center of the lens 100, and the second lens 120 (quartz glass) and the UVC lens placed at the accommodating space 130 are arranged at an interval from each other at the periphery of the lens 100.

It is to be noted that the human body sensing component 300 is placed at the center of the ceramic heat sink 230 of the light source assembly 200; the visible light chip 210 is placed at the periphery of the human body sensing component 300, and the light emitted by the visible light chip 210 corresponds to the first lens 110; the UVA chip 221 and the UVC chip 222 are arranged at an interval from each other at the periphery of the visible light chip 210 to allow the uniform emission of UV light, i.e., the light emitted by the UVA chip 221 corresponds to the second lens 120, and the light emitted by the UVC chip 222 corresponds to the UVC lens placed at the accommodating space 130.

In some embodiments, the control component 420 controls the on and off of the power supply component 410 by receiving the information fed by the human body sensing component 300, to enable different operating modes of the LED UV sterilization device, including a illumination mode, a sterilization mode, and a visible sterilization mode:

1) in the illumination mode, the control component 420 controls the visible light chip 211 of the visible light source assembly 210 to emit visible light; in this mode, the control component 420 does not respond when the human body sensing component 300 senses information from a human body or other living creatures, i.e., movements of a human body or other living creatures do not affect the operation of this mode.

2) In the sterilization mode, the control component 420 controls the UVA chip 221 and the UVC chip 222 of the ultraviolet light source assembly 220 to emit ultraviolet light; at this time, the ultraviolet light source assembly 220 controlled by the control component 420 may have the following operation modes: the UVA chip 221 works alone, the UVC chip 222 works alone, and the UVA chip 221 and the UVC chip 222 work together. In the sterilization mode, the control component 420 turns off the ultraviolet light source assembly 220 when the human body sensing component 300 senses information from a human body or other living creatures, i.e., movements of a human body or other living creatures will affect the operation in this mode, which can effectively prevent the UV light from causing harm to the human body or other living creatures.

(3) in the visible sterilization mode, the control component 420 controls the visible light chip 211 of the visible light source assembly 210 to emit visible light and controls the UVA chip 221 and/or the UVC chip 222 of the ultraviolet light source assembly 220 to emit ultraviolet light; in this mode, when the human body sensing component 300 senses information from a human body or other living creatures, the control component 420 turns off at least the ultraviolet light source assembly 220. For example, if illumination is not required at a specific time (e.g., when the device is operating during the day), the control component 420 turns off the visible light chip 211, the UVA chip 221 and the UVC chip 222; if illumination is required at a specific time (e.g., when the device is operating at night), the control component 420 only turns off the UVA chip 221 and the UVC chip 222.

Embodiment 2: The Combination of a Visible Light Chip with a Single UV Chip, Specifically "Visible Light Chip+UVC Chip" as an Example Specifically, the light source assembly 200 includes a visible light source assembly 210, an ultraviolet light source assembly 220, and a ceramic heat sink 230. The visible light source assembly 210 includes a visible light chip 211; the ultraviolet light source assembly 220 includes a UVC chip 222; the visible light chip 211 and the UVC chip 222 are placed on the ceramic heat sink 230.

It is to be noted that the human body sensing component 300 is placed at the center of the ceramic heat sink 230; the visible light chip 210 is placed at the periphery of the human body sensing component 300; and the UVC chip 222 is placed at the periphery of the visible light chip 210.

In some embodiments, the visible light chip 211 is an LED chip, the first lens 110 is preferably a PC lens, and the visible light emitted by the LED chip passes through the PC lens to form a visible beam d; the second lens 120 may be quartz glass or a special UVC lens, the ultraviolet light emitted by the UVC chip 222 passes through the quartz glass or UVC lens to form an ultraviolet beam e. The two beams (d and e) converge to form an overlapped spot on the surface to be irradiated (i.e., the area to be sterilized). At this time, visible light will indicate the irradiation position of the ultraviolet light, thus making the sterilization effect more effective and fast.

It should be noted that the first lens 110 and the second lens 120 may be integrated as a whole or may be separated structures.

In some embodiments, the control component 420 controls the on and off of the power supply component 410 by receiving the information fed by the human body sensing component 300, to enable different operating modes of the LED UV sterilization device, including a illumination mode, a sterilization mode, and a visible sterilization mode:

1) in the illumination mode, the control component 420 controls the visible light chip 211 of the visible light source assembly 210 to emit visible light; in this mode, the control component 420 does not respond when the human body sensing component 300 senses information from a human body or other living creatures, i.e., movements of a human body or other living creatures do not affect the operation of this mode.

2) in the sterilization mode, the control component 420 controls the UVC chip 222 of the ultraviolet light source assembly 220 to emit ultraviolet light; in this mode, the control component 420 turns off the ultraviolet light source assembly 220 when the human body sensing component 300 senses information from a human body or other living creatures, i.e., movements of a human body or other living creatures will affect the operation of this mode, which can effectively prevent the UV light from causing harm to the human body or other living creatures.

(3) in the visible sterilization mode, the control component 420 controls the visible light chip 211 of the visible light source assembly 210 to emit visible light and controls the UVC chip 222 of the ultraviolet light source assembly 220 to emit ultraviolet light; in this mode, when the human body sensing component 300 senses information from a human body or other living creatures, the control component 420 turns off at least the ultraviolet light source assembly 220. For example, if illumination is not required at a specific time (e.g., when the device is operating during the day), the control component 420 turns off the visible light chip 211 and the UVC chip 222; if illumination is required at a specific time (e.g., when the device is operating at night), the control component 420 only turns off the UVC chip 222.

Figure 3A:
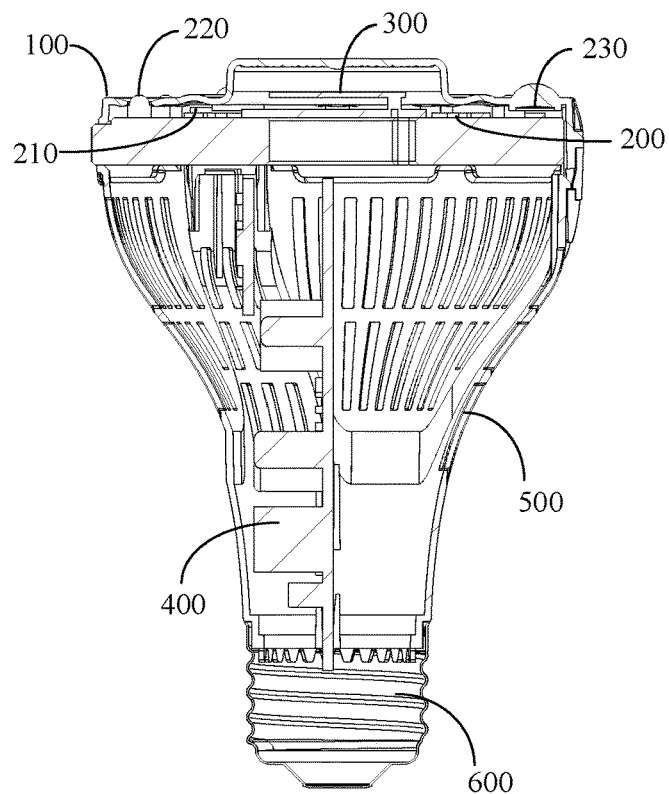
FIG. 3A is a schematic diagram showing the side section of an LED UV sterilization device according to an embodiment of the present disclosure.
Figure 3B:
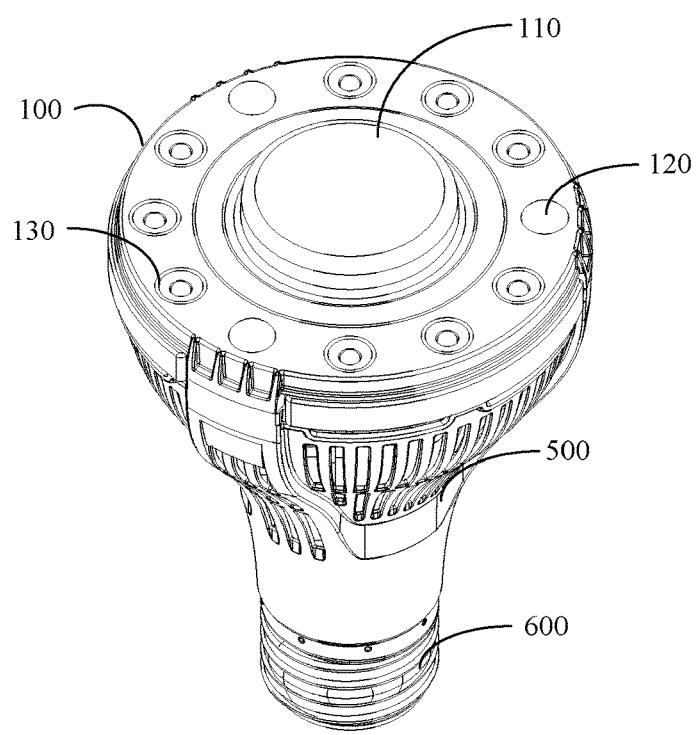
FIG. 3B is a schematic diagram showing the overall structure of an LED UV sterilization device according to an embodiment of the present disclosure.

FIG. 3A is a schematic diagram showing the side section of an LED UV sterilization device according to an embodiment of the present disclosure. FIG. 3B is a schematic diagram showing the overall structure of an LED UV sterilization device according to an embodiment of the present disclosure.

Specifically, the LED UV sterilization device of the present disclosure further includes a lamp housing assembly 500 and a lamp cap assembly 600. The lamp housing assembly 500 is designed as a pear-shaped structure with an accommodation chamber inside. The smooth lines of the lamp housing assembly 500 allow for better heat dissipation, while the structure is more compact and beautiful.

The power driving assembly 400 is placed within the accommodation chamber of the lamp housing assembly 500. The lamp cap assembly 600 may be removably connected to the lamp housing assembly 500; the above removable connection may include but is not limited to threaded connection, clamping connection, snap-on connection, welded connection, bonded connection, screwed connection, magnetic connection, etc. Combined with FIG. 1, the lens assembly 100 and the light source assembly 200 may be removably connected to each other; the above removable connection may include but is not limited to clamping connection, snap-on connection, welded connection, bonded connection, threaded connection, screwed connection, magnetic connection, etc. After the lens assembly 100 is connected to the power supply assembly 200, the snap part on the lens assembly 100 is connected to the snap part on the lamp housing assembly 500, thereby allowing the entire LED UV sterilization device to be assembled together. The removable connection facilitates subsequent disassembly for maintenance and installation.

In summary, the present disclosure provides a LED UV sterilization device, which not only realizes safe disinfection and sterilization, but also visualizes the sterilization process. The sterilization process is safer and more reliable, and the sterilization area is more accurate. By means of the optical structure of the sterilization device of the present disclosure, the light spot generated by the UV chip and the light spot generated by the visible light chip can basically be overlapped within a reasonable range by optical cooperation. During the disinfection and sterilization process, users can judge the UV sterilization area based on the visible light spot to realize accurate sterilization, thus improving the safety and effectiveness.

As mentioned above, the present disclosure effectively overcomes various shortcomings in the existing technology and has high industrial utilization value.

The above-mentioned embodiments are merely illustrative of the principle and effects of the present disclosure instead of limiting the present disclosure. Modifications or variations of the above-described embodiments may be made by those skilled in the art without departing from the spirit and scope of the disclosure. Therefore, all equivalent modifications or changes made by those who have common knowledge in the art without departing from the spirit and technical concept disclosed by the present disclosure shall be still covered by the claims of the present disclosure.

What is claimed is:

1. A light-emitting diode (LED) ultraviolet (UV) sterilization device, comprising:
    a lens assembly, including a plurality of lenses of different materials suitable for light of different wavelengths; and
    a light source assembly, including a visible light source assembly and an ultraviolet light source assembly; wherein visible light irradiated by the visible light source assembly and invisible ultraviolet light irradiated by the ultraviolet light source assembly pass through lenses of corresponding materials and form an overlapped light spot, so that an irradiation location of the invisible ultraviolet light is indicated by the visible light;
    wherein the visible light source assembly comprises a visible light chip; the ultraviolet light source assembly comprises a UVA chip and a UVC chip; wherein the lens assembly is reserved with an accommodating space for placing a UVC lens suitable for the UVC chip.

2. The LED UV sterilization device according to claim 1, wherein the lens assembly includes a first lens and a second lens;
    wherein the first lens is used for visible light transmission, and a material of the first lens includes any one of polycarbonate (PC), polymethyl methacrylate (PMMA), and glass; and the second lens is used for ultraviolet light transmission, and a material of the second lens includes quartz glass.

3. The LED UV sterilization device according to claim 1, further comprising a human body sensing component and a control component; wherein the control component is electrically connected to the human body sensing component; and when the human body sensing component senses human body information, the information is fed back to the control component, so that the control component controls the ultraviolet light source assembly not to Page 2 emit UV light.

4. The LED UV sterilization device according to claim 3, wherein an operating mode of the LED UV sterilization device includes an illumination mode, a sterilization mode, and a visible sterilization mode; wherein
    in the illumination mode, the visible light source assembly emits visible light, and in this mode, the control component does not respond when the human body sensing component senses human body information;
    in the sterilization mode, the ultraviolet light source assembly emits ultraviolet light, and in this mode, the control component turns off the ultraviolet light source assembly when the human body sensing component senses human body information;

in the visible sterilization mode, the visible light source assembly emits visible light, and the ultraviolet light source assembly emits ultraviolet light; in this mode, the control component turns off at least the ultraviolet light source assembly when the human body sensing component senses human body information.

5. The LED UV sterilization device according to claim 4, wherein the human body sensing component comprises an infrared sensor and/or a radar sensor.

6. The LED UV sterilization device according to claim 1, wherein the light source assembly further comprises a ceramic heat sink for placing a chip of the light source assembly.

7. The LED UV sterilization device according to claim 1, further comprising a lamp housing assembly and a lamp cap assembly.

* * * * *